(12) United States Patent
Davydov et al.

(10) Patent No.: US 10,085,815 B2
(45) Date of Patent: Oct. 2, 2018

(54) METHOD FOR PERFORMING STEREOTACTIC BRAIN SURGERY USING 3D GEOMETRIC MODELING

(71) Applicant: Albert Davydov, Forest Hills, NY (US)

(72) Inventors: Albert Davydov, Forest Hills, NY (US); Peter Usov, Belle Mead, NJ (US)

(73) Assignee: Albert Davydov, Forest Hills, NY ( * ) Notice: Subject to any disclaimer, the term of this patent is extended or adjusted under 35 U.S.C. 154(b) by 38 days.

(21) Appl. No.: 15/444,411

(22) Filed: Feb. 28, 2017

(65) Prior Publication Data
US 2017/0172690 A1    Jun. 22, 2017

Related U.S. Application Data

(63) Continuation-in-part of application No. 14/808,880, filed on Jul. 24, 2015, now Pat. No. 9,579,046.

(51) Int. Cl.
*A61B 90/00*        (2016.01)
*A61B 90/50*        (2016.01)
(Continued)

(52) U.S. Cl.
CPC ............ *A61B 90/14* (2016.02); *A61B 5/0077* (2013.01); *A61B 5/1077* (2013.01);
(Continued)

(58) Field of Classification Search
None
See application file for complete search history.

(56) References Cited

U.S. PATENT DOCUMENTS 5,971,997 A * 10/1999 Guthrie .................. A61B 90/11
606/130
7,077,822 B1 * 7/2006 Howard, III ......... A61N 1/0529
600/378
(Continued)

FOREIGN PATENT DOCUMENTS

JP    2006238974 A  *  9/2006  ............. G06T 19/00

OTHER PUBLICATIONS

JP 2006-238974 A [machine translation].*

*Primary Examiner* — Michelle M Entezari
(74) *Attorney, Agent, or Firm* — Anna Vishev

(57) ABSTRACT

A method for performing a stereotactic brain surgery. The method includes first interposing a left and a right anthropological baselines on a patient's face, each trago-orbital anthropological baseline connecting an orbitale point and an auricular point on a corresponding side of the patient's face. A headgear unit having a pair of temple elements and a front housing, where the front housing includes at least two cameras and a 3D compass, is then positioned on a patient's head. Each of the two cameras is adjusted such that its view field picks up one of the two trago-orbital anthropological baselines on the patient's face. These view fields of the two cameras are then used to construct a Human Skull Base Plane as a plane formed by the left and right anthropological baselines when these anthropological baselines are parallel and aligned. The same view fields of the two cameras are also used to identify a precise center of the patient's face, and a center of the front housing is then positioned in alignment with the center of the patient's face. The 3D compass is then positioned into a measuring plane coinciding with the Human Skull Base Plane, and is used to quantitatively measure a three-dimensional orientation of the patient's head at the time when the 3D compass is positioned within the measuring plane coinciding with the (Continued)

constructed Human Skull Base Plane. An image of a patient's brain is then obtained and stored in correlation with the measured three-dimensional orientation of the patient's head. Prior to the surgery, the patient's head is positioned into the same position in which the image was taken. A stereotactic brain surgery is then performed using the stored image.

2 Claims, 6 Drawing Sheets

(51) Int. Cl.
*A61B 5/00* (2006.01)
*A61B 5/107* (2006.01)
*A61B 5/11* (2006.01)
*A61B 90/14* (2016.01)
*G06T 7/73* (2017.01)
*H04N 13/243* (2018.01)
*H04N 13/02* (2006.01)

(52) U.S. Cl.
CPC .......... *A61B 5/1079* (2013.01); *A61B 5/1122* (2013.01); *A61B 5/1128* (2013.01); *A61B 5/6803* (2013.01); *A61B 90/361* (2016.02); *A61B 90/37* (2016.02); *G06T 7/74* (2017.01); *H04N 13/0242* (2013.01); *H04N 13/243* (2018.05); *A61B 2090/371* (2016.02); *A61B 2090/502* (2016.02); *G06T 2207/10028* (2013.01); *G06T 2207/30016* (2013.01); *G06T 2207/30196* (2013.01)

(56) References Cited

U.S. PATENT DOCUMENTS

| | | | |
|---|---|---|---|
| 2008/0051651 A1* | 2/2008 | Yamamoto | A61B 8/08 600/437 |
| 2011/0270084 A1* | 11/2011 | Choi | A61B 34/20 600/427 |
| 2014/0369584 A1* | 12/2014 | Fan | A61B 6/501 382/131 |
| 2017/0090220 A1* | 3/2017 | Bonnin | G02C 13/005 |
| 2017/0312064 A1* | 11/2017 | Jaisson | A61C 19/045 |

* cited by examiner

METHOD FOR PERFORMING STEREOTACTIC BRAIN SURGERY USING 3D GEOMETRIC MODELING

BACKGROUND OF THE INVENTION

This application and its disclosure generally relate to the field of determining orientation of a human head in three-dimensional geometric modeling and then using this orientation in stereotactic brain surgery.

Head orientation measurements in 3D geometric modeling are currently based on a combination of measurements determined by different gyroscopes, accelerometers and electronic compasses. For example, one such system is based on measurements provided by a three-axis accelerometer and a resonator gyroscope mounted on a headgear.

Other methods and measuring systems, currently in use, utilize dual inclinometers, bubble goniometers, radiographs, compass technology, visual estimation, ultrasound, geometric methods, digital optoelectronic instruments, computerized kinematic analysis using passive markers and infrared TV cameras, MRI or sensors attached to the subject's head for head orientation determination. However, none of the existing methods yield a sufficient accuracy in defining the neutral position of a human head in three-dimensions.

This lack of a precise definition of the neutral position of the 3D orientation of the human head is a serious disadvantage in current 3D geometric modeling, especially when one needs to determine some specific measurements and orientation of the human head during motion. In certain applications, for example in dental arts and in stereotactic brain surgery, the existing methods result in significant errors and distortions in the subject's measurements and, consequently, in the resulting 3D model.

A stereotactic brain surgery is a surgical procedure where lesion, frequently, a brain tumor, is removed with the assistance of image guidance. Images used in this process are typically obtained prior to the surgery to allow the surgeon to study the exact location of the lesion and to develop a surgical plan, i.e., to create a pathway through the brain for safe removal of as much abnormal tissue as possible while leaving normal, healthy brain relatively intact. Stereotactic brain surgery is typically performed with a computer system which integrates an image obtained through a special MRI or CT performed one or two days before the surgery. This image is then imported into the computer system which provides doctors with a 3-dimensional image of the subject's brain and of the intended target. Surgeons later use this image to guide their removal of the target lesion. In order to obtain the image and to subsequently to perform the surgery, a neurosurgical head holder (skull clamp) system is used to secure the patient's head position during surgical procedures. The system may include a head holder frame that attaches to the operating table, skull clamp, neurosurgical head hold stabilization components, skull pins and other accessories. Because, positioning of the neurosurgical head holder during image taking does not exactly correspond to its positioning during the surgery, and, generally, is not 100% precise every time, the image on the computer system often does not precisely coincide with the actual brain topography at the surgeon's table. Because the surgeon relies on this image during the surgery, this imprecision sometimes results in severe damage to the patient's brain.

SUMMARY OF THE INVENTION

It is an object of the present invention to provide a method of performing head motion and orientation measurements that are accurate, reliable, user-friendly and portable with low-cost.

It is also an object of the present invention to provide a method of using the obtained orientation measurements to perform stereotactic brain surgery.

In its general aspect, the invention is a method for performing stereotactic brain surgery. The method includes first interposing a left and a right trago-orbital anthropological baselines on a patient's face, each trago-orbital anthropological baseline connecting an orbitale point and an auricular point (Tragus) on a corresponding side of the patient's face. A headgear unit having a pair of temple elements and a front housing attached to the temple elements, where the front housing includes at least two cameras and a 3D compass, is then positioned on a patient's head. Each of the two cameras is adjusted such that its view field picks up one of the two trago-orbital anthropological baselines on the patient's face. These view fields of the two cameras are then used to construct a Human Skull Base Plane as a plane formed by the left and right trago-orbital anthropological baselines when these anthropological baselines are parallel and aligned. The same view fields of the two cameras are also used to identify a precise center of the patient's face, and a center of the front housing is then positioned in alignment with the center of the patient's face. The 3D compass is then positioned into a measuring plane coinciding with the Human Skull Base Plane, and is used to quantitatively measure a three-dimensional orientation of the patient's head at the time when the 3D compass is positioned within the measuring plane coinciding with the constructed Human Skull Base Plane. An image of a patient's brain is then obtained and stored in correlation with the measured three-dimensional orientation of the patient's head. Prior to the surgery, the patient's head is positioned into the same position in which the image was taken. A stereotactic brain surgery is then performed using the stored image.

BRIEF DESCRIPTION OF THE DRAWINGS

The invention is illustrated by way of examples which are not a limitation, and the figures of the accompanying drawings in which references denote corresponding parts, and in which.

DETAILED DESCRIPTION OF THE INVENTION

As illustrated the attached Figures, the method and apparatus of the present invention are used to determine a correct neutral position of the 3d orientation of a human head. Once such correct neutral position is determined, it can be used for an unambiguous definition of the 3D orientation of the human head and for head orientation during motion.

Figure 2:
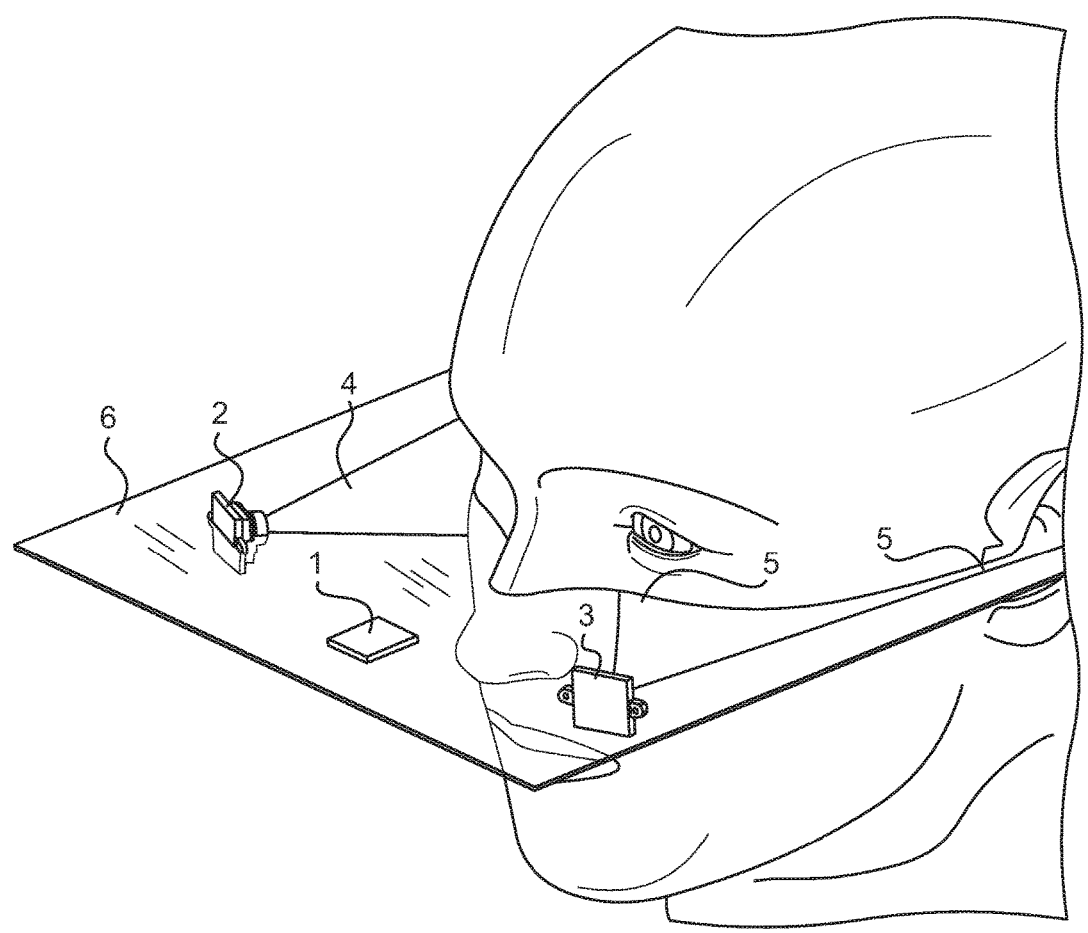
FIG. 2 is a schematic diagram of the geometric principles applicable to the present invention.
Figure 3:
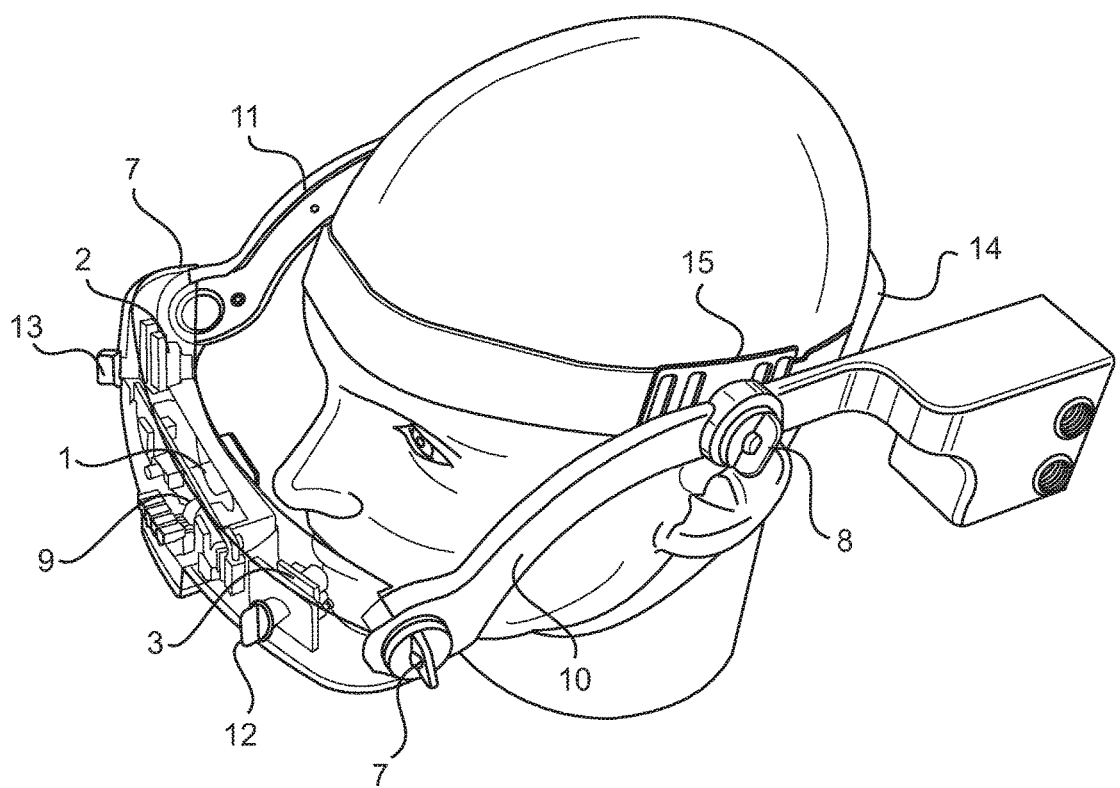
FIG. 3 is a schematic diagram of the apparatus for unambiguously determining orientation of a human head in 3d geometric modeling in accordance with one embodiment of the present invention.

Elements of the apparatus for determining the correct neutral position of the 3d orientation of human head are shown in FIGS. 2-3. In accordance with the preferred embodiment, the headgear unit 100 has a plastic frame 16 with two temple elements 10, 11 and a front housing 18. At least one 3D compass 1 with its electronic hardware 9 are secured within the front housing 18. The 3D compass 1 is an integrated compass module for heading computation and calibration of magnetic distortions. The module combines 3-axis magneto-resistive sensors and 3-axis micro electromechanical systems accelerometers, analog and digital support circuits. This set of compasses is intended to measure magnetic fields. A more detailed description of the compass components is provided below with respect to FIG. 4.

The headgear unit 100 further includes an adjustable headband 14 positionable on a patient's head. Frame 16 is secured to the headband 14 through clips 15 and pivot posts 8 located on each side of the headband. The frame is secured in such a way that it pivots on the posts 8 under friction with respect to the headband. Both clips 15 and pivot posts 8 can be provided in various sizes to accommodate different head sizes.

The front housing 18 also includes at least one pair of cameras, i.e., the left camera 2 and a right camera 3. The entire unit 100 can tilt slightly up or down to align the right and left cameras with the anthropological base lines. The horizontal positioning of each camera can also be adjusted and fixed using pivotable knobs 12 and 13 securing the cameras to the front housing 18. Pivotable knobs 12 and 13 are movable along the slots 19 (more clearly shown in FIG. 5). Thus, to adjust the horizontal positioning of each camera, the user will loosen the corresponding knob without detaching it from the camera, move the knob with the camera into a new desired position, and then screw the knob into place fixing the camera in the new position. Further, the entire front housing is attached to the temple elements 10, 11 with frontal knobs 7 allowing the front housing 18 with its cameras 2, 3 and 3D compass 1 to move with respect to the temple elements and without changing the position of such temple elements.

Figure 5:
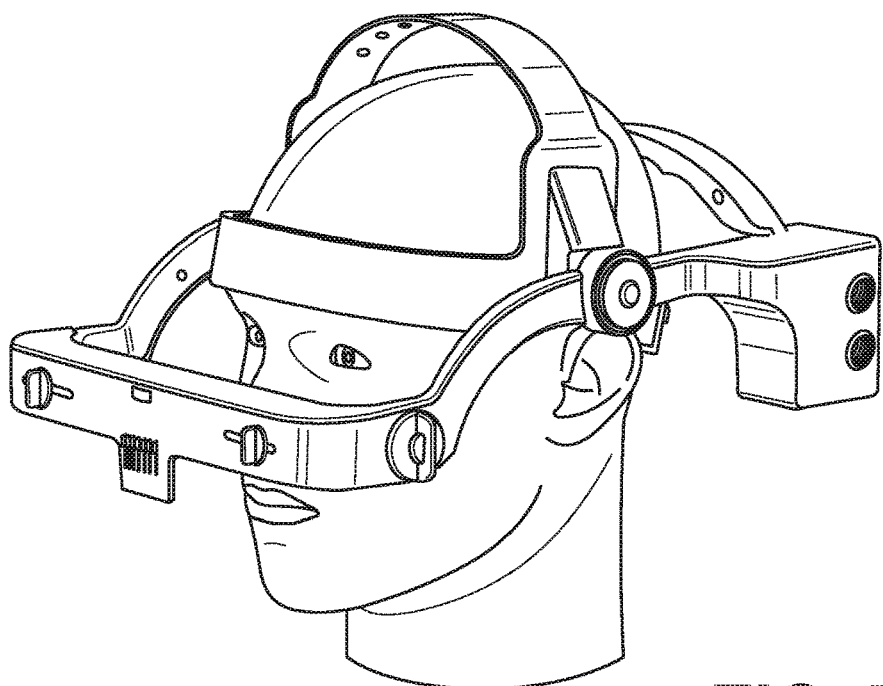
FIG. 5 is a schematic diagram of a first alternative embodiment of the headgear apparatus.
Figure 6:
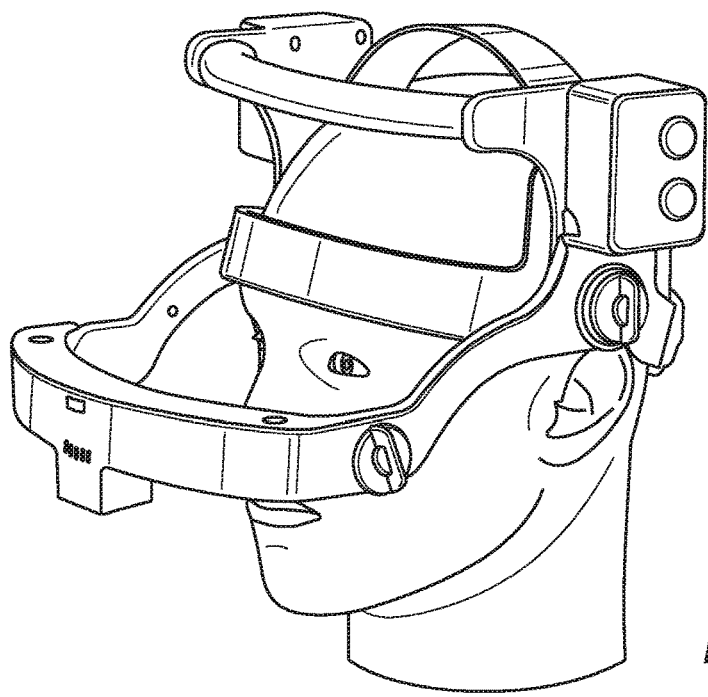
FIG. 6 is a schematic diagram of a second alternative embodiment of the headgear apparatus.
Figure 7:
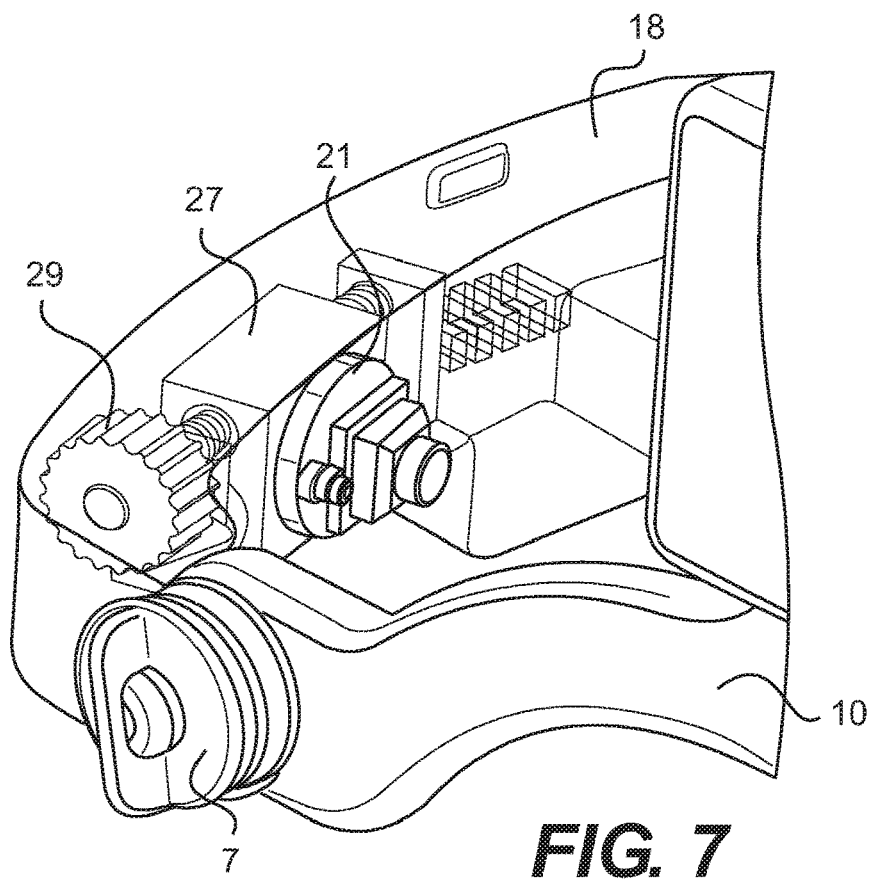
FIG. 7 is a schematic diagram of a portion of the headgear apparatus.
Figure 8:
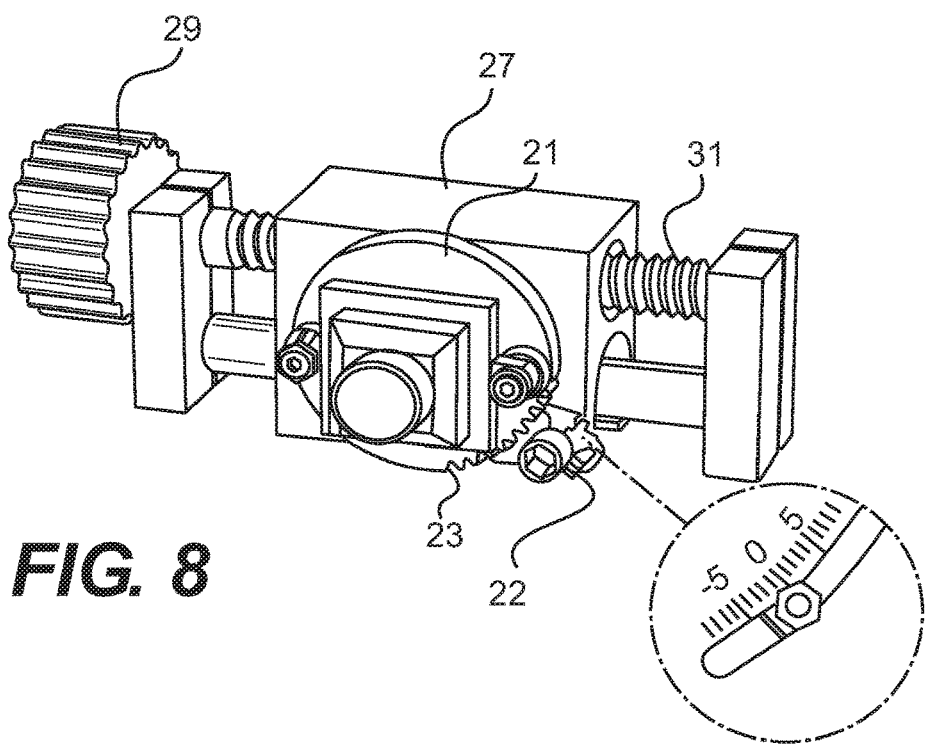
FIG. 8 is a schematic diagram of the camera mounting of the headgear apparatus.

Two alternative embodiments of the headgear apparatus are shown in FIGS. 5 and 6. As shown in FIG. 5, in addition to the elements described above with respect to headgear unit 100, headgear unit 102 includes a first arched component 32, connecting the end portions of the temple elements 10 and 11, and a second arched component 34, connected to both temple elements in the region of the pivot posts 8 and forming a part of the headband 14. Headband 14, in this embodiment (as well as in the embodiment shown in FIG. 6), includes a pair of support portions 38, extending over the second arched component 34 so as to attach and support the headband on the second arched component As shown in FIG. 6, headgear unit 104, in accordance with the second alternative embodiment, also includes the first arched component 32 and the second arched component 34. In this embodiment, however, first arched component 32 is positioned above the patient's head, and temple elements 10 and 11 are shortened. The headband 14 is secured on the patient's head with a clip 33. The entire frame 16 is pivotable around pivot posts 8 to adjust the angular position of the frame with respect to the headband and the patient's head. This embodiment provides more comfort for the patient and easier accessibility for the technician. Additionally, in this embodiment, cameras are secured differently within the front housing 18. The mechanism for securing the cameras within the front housing is more particularly shown in FIGS. 7-8. Each camera is preferably secured to a disk 21 having a set of teeth 23 connected to a gear 25. By rotating the gear 25, the user can adjust the angular position of the disk and, consequently, of the corresponding camera. Further, the disk is preferably positioned on a movable base 27. Screws 29 with their posts 31 have a worm-type connection with the movable base 27 such that, when the screw head is rotated, the movable base moves horizontally along the post 31. As shown in FIG. 6, a portion of the screw head of each screw 29 preferably protrudes above the top surface of the front housing 18. Thus, to adjust the horizontal positioning of the camera, a user will rotate the corresponding screw head, moving the corresponding base 27 into a desired position. This embodiment allows the user to adjust the horizontal positioning of the cameras in very small incremental steps, thus, resulting in higher accuracy of the measurements.

Figure 4:
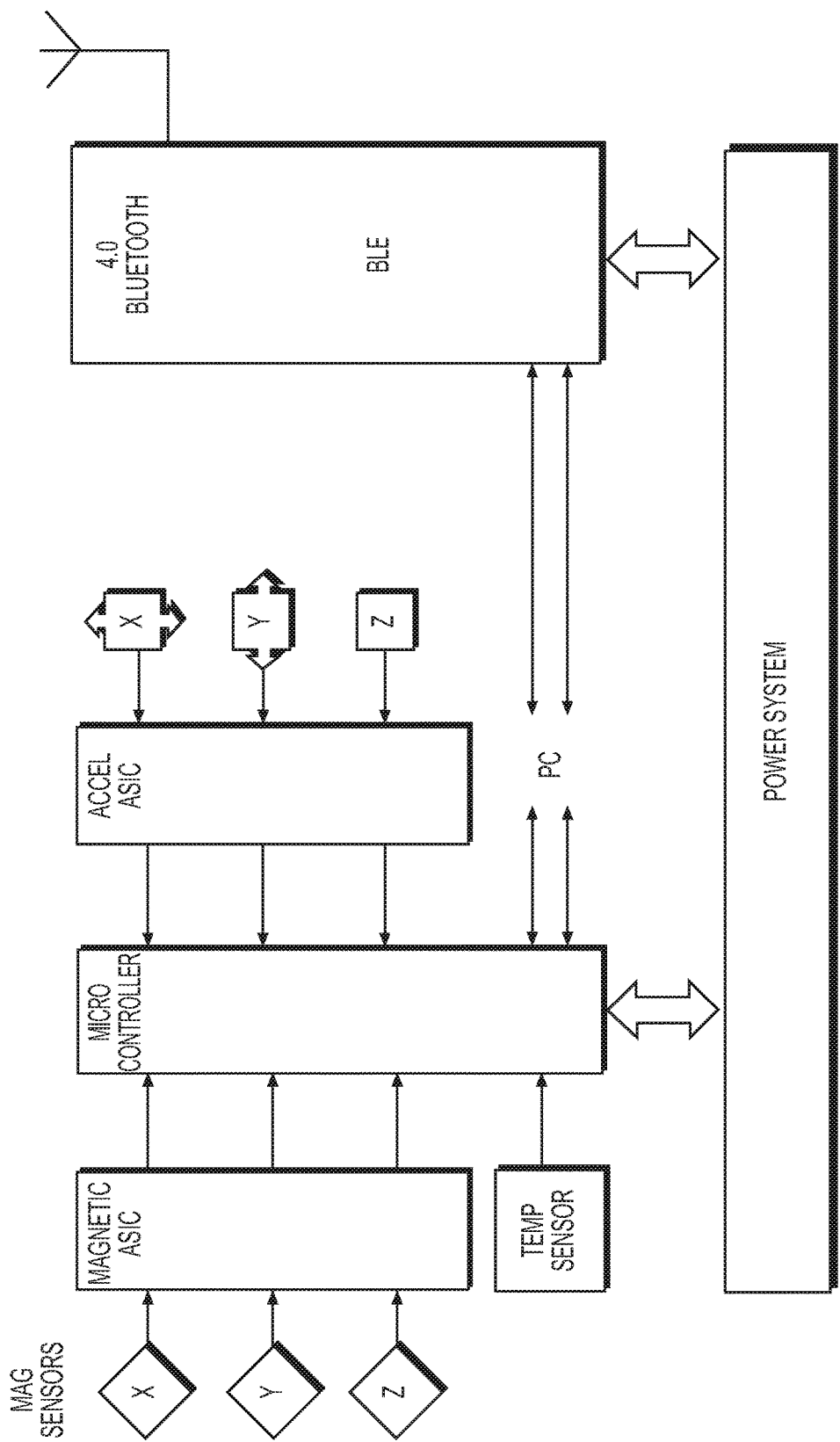
FIG. 4 is a schematic diagram of the electronic components of the 3d compass.

The electronic components of the hardware 9 are shown in FIG. 4. In accordance with the preferred embodiment, the electronic hardware includes a plurality of sensors, i.e., the 3-axis magnetic sensors 20 and 3-axial accelerometer 22, a microcontroller 24 connected to and receiving signals from the sensors 20 and 22, a power system 26 (e.g., a battery) powering all the components of the hardware, and an RF transceiver module 28.

Microcontroller 24 is integrated for computation of direction and calibration of signals from 3D compass sensors 20 and 22. It provides solid-state construction with very low cross-axis sensitivity designed to measure both direction and magnitude of Earth's magnetic fields. Power system 26 provides power to all components. With power supply applied, the sensors convert any incident magnetic field in the sensitive axis direction to a differential voltage output. RF transceiver module 28 (designated as BLE 4.0 Bluetooth® in FIG. 4) is preferably a low-power 2.4 GHz Bluetooth® 4.0 (BLE) System-on-Chip as a single mode Bluetooth Smart module that complies with Bluetooth Core Specification v4.1. It integrates RF, a baseband controller, command API processor that implements the Bluetooth Generic Attribute Profile.

Data generated by the 3D compass with its electronic hardware is a processed data that can be transmitted to any computing device, preferably wirelessly, for further processing and/or displaying on a monitoring screen. In the preferred embodiment, the 3D compass with its electronic hardware is wirelessly connected to a computer software using an energy-efficient reliable data transfer protocol, thereby limiting the potential errors and default settings. Furthermore, the personal computer software is able to display specific instructions to the user, in order to insure proper measurement techniques and to limit inter-user errors.

Figure 1:
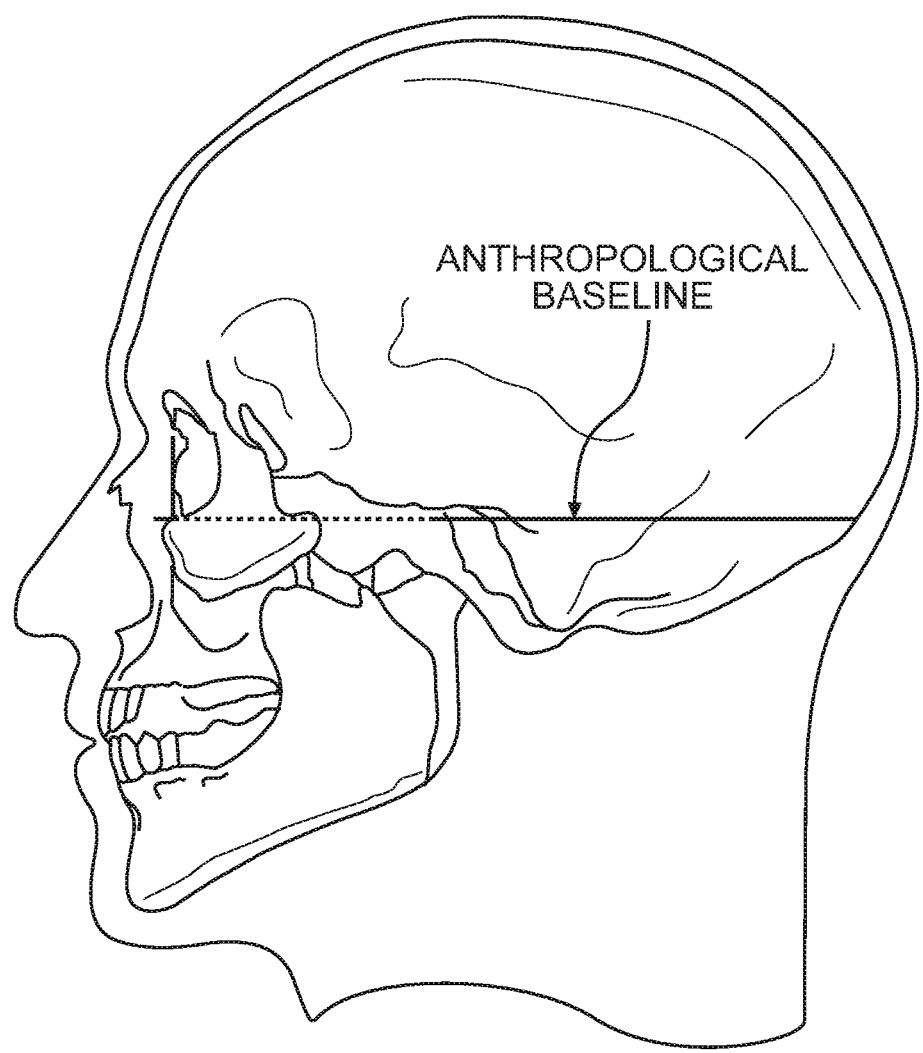
FIG. 1 is a schematic diagram of a human skull showing the anthropological baseline.

In accordance with the preferred method of the present invention the 3D compass is installed into the horizontal plane perpendicular to the sagittal plane and is rotated until the horizontal plane of the sensor is parallel to and aligned with the Human Skull Base Plane. The Human Skull Base Plane is a plane passing through the left and right anthropological baselines of a human skull. As shown in FIG. 1, the anthropological baseline as a line drawn from the inferior margin of the orbit (Orbitale point) to the auricular point (center of the orifice of the external acoustic meatus, Auricular point on the Tragus) and extending backward to the center of the occipital bone. In accordance with the preferred embodiment of the present invention, the left and right trago-orbital anthropological baselines are actually drawn on the patient's face to be picked up by the cameras. However, any other known technique for interposing the line onto the patient's face may be utilized, e.g., connecting the orbitale point to the auricular point with a ray of light projected onto the face.

Precise centering of the frame (PCF) of the headgear unit is performed after the trago-orbital anthropological lines are interposed. One way of performing PCF is by using lateral angles of the patient's eyes. The images of the lines above include the images of the lateral angles of the eyes. First, the lateral angles of both eyes on the image seen on the monitor are marked using measuring software. Second, using the software guidance, the operator positions the headgear unit such that the center of its frame coincides with the precise center of the face. Finally, once the operator places the frame of the headgear unit into the alignment with the exact center, the operator saves the data and can start closing the dials of headband on the head.

The following are the geometric principles of the present method of determining a neutral position of 3D orientation of a human head. The 3D compass 1 in accordance with its predetermined algorithm is placed into the horizontal plane created perpendicular to the sagittal plane of the human head and is rotated until this horizontal plane is parallel to and aligned with the Human Skull Base Plane 6. The correct position of the compass 1 is controlled by the two cameras 2 and 3 located on the left and on the right sides, respectively, and PCF as described above. As shown in FIG. 2, each camera is placed perpendicular to the Human Skull Base Plane 6 and such that cameras' view angles 5 and 4 pick up the left and right anthropological baselines interposed on the patient's face. The cameras then digitize the signals and transmit them to a video monitor (not shown). When the picked up images of the two anthropological baselines are parallel and aligned, the plane passing through the two lines is the Human Skull Base Plane 6.

If images of the anthropological baselines of human skull on the video monitor run parallel to the X-axis and lie on the same line, then cameras 2 and 3 are set correctly. The 3D compass 1 lies on the plane perpendicular to the (vertical) Y-axis of cameras and lies in the same plane as the Human Skull Base Plane 6. This plane of the 3D compass is referred to as the measuring plane, and the position of the 3D compass 1 in this measuring plane is recorded as the correct neutral position of the patient's 3D head orientation.

As explained above, the present invention provides a computational model for determining a correct neutral position of 3D human head orientation. When the 3D compass 1 is oriented and mounted along the Human Skull Base Plane 6, the signal from the compass sensor is preferably transferred to a computer system which records this neutral position. Each movement of the patient's head thereafter is recorded and measured as relative to the recorded neutral position. Thus, all further 3D motions and orientations of the patient's head are measured with respect to an objective, neutral and independent parameter, allowing for further 3D modeling. Moreover, once the neutral position of a human skull is determined, by placing sensors on other body parts, positions and parameters of these other body parts can be accurately measured with respect to the determined neutral parameters (i.e., the anthropological baseline). For example, by placing additional sensors on a cervical spine of the patient, and recording the positions of such sensors with respect to the neutral position determined by the 3D compass, it is possible to measure various ranges of motion of the cervical spine of the patient. Based on an empirical study, the method and system of the present invention allow its user to make measurements with resulting accuracy of approximately 0.5°.

The accurate 3D modeling based on the method described herein is particularly advantageous in the following industries:

Dentistry, Orthodontics
Dentistry, Prosthodontics
Dentistry, Maxillofacial Surgery
Robotic Geriatric Patient Care
Robotic Surgical/Treatment Assistant
Robotic Surgery
General Radiology
Radiation Oncology
Physical Medicine and Rehabilitation: Orthopedic Rehabilitation Devices for Spinal Column
Toys and Video Games
Aero Space and Machinery Operators Training Systems
Imitation of Disaster Situations and Training for their Mitigations (Accidents, car accidents, etc.)
Simulation Systems of Human Body
Human Body LPS (Local Position System)
High Precision Military Robotic Systems
High Accuracy Head Based Aiming Systems
Dentistry, TMJ Metric Analysis
Dentistry, TMJ orthotics and
Sleep Apnea Appliances planning and fabrication Specifically, to perform a stereotactic brain surgery, a user first determines orientation of the patient's head in three-dimensional geometric modeling using the above described method. Next, an image of the patient's brain is obtained in this determined orientation. The image is then stored in a computer system in correlation with the determined orientation. This image can then be studied by a surgeon to develop a surgical plan. Prior to performing stereotactic brain surgery, the previously determined orientation of the patient's head is used to position the patient's head for the surgery into the same position as the position used for taking the image. The surgeon can then perform the stereotactic brain surgery with a high level of precision.

In the preceding specification, the invention has been described with reference to specific exemplary embodiments thereof. It will however, be evident that various modifications and changes may be made thereto without departing from the broader spirit and scope of the invention as set forth in the claims that follow. The specification and drawings are accordingly to be regarded in an illustrative manner rather than a restrictive sense.

We claim as follows:

1. A method for performing a stereotactic brain surgery comprising the steps of:
   interposing a left and a right anthropological baselines on a patient's face, each trago-orbital anthropological baseline connecting an orbitale point and an auricular point on a corresponding side of the patient's face;
   providing a headgear unit comprising a pair of temple elements and a front housing, said front housing including at least two cameras and a 3D compass;
   positioning the headgear unit on a patient's head;
   positioning each of said two cameras such that its view field picks up one of said anthropological baselines on the patient's face;
   using the view fields of said two cameras to construct a Human Skull Base Plane as a plane formed by said left and right trago-orbital anthropological baselines when said trago-orbital anthropological baselines are parallel and aligned;

using the view fields of said two cameras to identify a precise center of the patient's face and positioning a center of said front housing in alignment with the center of the patient's face;

positioning said 3D compass into a measuring plane coinciding with the constructed Human Skull Base Plane;

using said 3D compass to quantitatively measure a three-dimensional orientation of the patient's head at the time when said 3D compass is positioned within the measuring plane coinciding with the constructed Human Skull Base Plane;

taking an image of a patient's brain in a first position;

storing said image of the patient's brain in correlation with said measured three-dimensional orientation of the patient's head;

positioning the patient's head into said first position in which said image was taken and performing a stereotactic brain surgery using said stored image.

2. The method for performing a stereotactic brain surgery according to claim 1, wherein said step of positioning the patient's head into said first position is performed using said headgear unit.

* * * * *